US 8,857,983 B2

(12) United States Patent
Pugh et al.

(10) Patent No.: US 8,857,983 B2
(45) Date of Patent: Oct. 14, 2014

(54) OPHTHALMIC LENS ASSEMBLY HAVING AN INTEGRATED ANTENNA STRUCTURE

(75) Inventors: Randall Braxton Pugh, St. Johns, FL (US); Daniel B. Otts, Fruit Cove, FL (US); Frederick A. Flitsch, New Windsor, NY (US); Adam Toner, Jacksonville, FL (US); Scott Robert Humphreys, Greensboro, NC (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/358,579

(22) Filed: Jan. 26, 2012

(65) Prior Publication Data

US 2013/0194540 A1 Aug. 1, 2013

(51) Int. Cl.
*G02C 7/08* (2006.01)
*G02C 7/04* (2006.01)

(52) U.S. Cl.
CPC . *G02C 7/083* (2013.01); *G02C 7/04* (2013.01)
USPC ............. 351/159.39; 351/159.03; 623/6.22

(58) Field of Classification Search
CPC . A61F 2/1635; A61F 2250/0002; H01Q 1/22; H01Q 1/2225; H01Q 7/00; G02C 7/04; G02C 7/083
USPC ............ 351/159.01–159.03, 159.39–159.4; 623/6.11–6.62
See application file for complete search history.

(56) References Cited

U.S. PATENT DOCUMENTS

| 4,787,903 A | 11/1988 | Grendahl |
| 4,816,031 A | 3/1989 | Pfoff |
| 5,596,567 A | 1/1997 | deMuro et al. |
| 7,548,040 B2 | 6/2009 | Lee et al. |
| 2006/0095128 A1* | 5/2006 | Blum et al. .................. 623/6.37 |
| 2007/0128420 A1* | 6/2007 | Maghribi ...................... 428/221 |
| 2008/0058652 A1* | 3/2008 | Payne ............................ 600/488 |
| 2009/0033863 A1* | 2/2009 | Blum et al. ................. 351/160 R |
| 2009/0182426 A1* | 7/2009 | Von Arx et al. ............. 623/11.11 |
| 2009/0244477 A1 | 10/2009 | Pugh et al. |
| 2010/0103369 A1 | 4/2010 | Pugh et al. |

FOREIGN PATENT DOCUMENTS

| DE | 19858172 A1 | 6/2000 |
| DE | 10207048859 A1 | 4/2009 |
| WO | WO 94/23334 A1 | 10/1994 |
| WO | WO 2006/050171 A2 | 5/2006 |
| WO | WO 2008/091859 A1 | 7/2008 |
| WO | WO 2008/109867 A2 | 9/2008 |

OTHER PUBLICATIONS

Pandey, J.; Yu-Te Liao; Lingley, A.; Mirjalili, R.; Parviz, B.; Otis, B.P., "A Fully Integrated RF-Powered Contact Lens With a Single Element Display," Biomedical Circuits and Systems, IEEE Transactions on, vol. 4, No. 6, pp. 454,461, Dec. 2010.*

(Continued)

*Primary Examiner* — Darryl J Collins
*Assistant Examiner* — Gary O'Neill
(74) *Attorney, Agent, or Firm* — Carl J. Evens

(57) ABSTRACT

Antennas and antenna systems may be designed and configured for incorporation into mechanical devices, including medical devices, such as ophthalmic devices, including contact lenses. These antennas and antenna systems may be utilized to transmit data from the mechanical device to a receiver, to receive data from a transmitter, and/or to inductively charge an electromechanical cell or the like incorporated into the mechanical device.

5 Claims, 18 Drawing Sheets

(56) References Cited

OTHER PUBLICATIONS

Loy, M., et al., "ISM-Band and Short Range Device Antennas", Texas Instruments Application Report, Aug. 2005. Online: http://www.ti.com/lit/answra046a/.

Pandey, J., et al. "Toward an Active Contact Lens: Integration of a Wireless Power Harvesting IC", Dept. of Elect. Eng., University of Washington, Seattle, WA, USA. Biomedical Circuits and Systems Conference, 2009. BioCAS 2009. IEEE Issue Date: Nov. 26-28, 2009 pp. 125-128 online: http:/wireless.ee.washington.edu/papers/biocas2009 inpyudodpo.pdf.

Parviz, B., "Augmented Reality in a Contact Lens", IEEE Spectrum, Sep. 2009. Online: http:/spectrum.ieee.org/biomedical/bionics/augmented-reality-in-a-contact-lens/O.

Williams, A. "Swiss Startup Puts MEMS Sensor in Contact Lens", Electronics Weekly.com, Mar. 25, 2010, 9:29 AM online: http://www.electronicsweekly.com/blogs/uk-technology-startups/2010/03/swiss-startup-puts-mems-sensor.tml.

Davies, C., "Opto-Electronic Contact Lenses Promise Wireless Displays", Nov. 25, 2009. Online: http://www.slashgear.com/opto-electronic-contact-lenses-promise-wireless-displays-2564454/.

Orca, Surfdaddy, "Micro Machines and Opto-Electronics on a Contact Lens", Nov. 20, 2009. Online: http://www.hplusmagazine.com/arraicles/toys-tools/micro-machines-and-opto-electortncis-contact-lense.

Parviz, Babak, A., "Augmented Reality in a Contact Lens, A New Generation of Contact Lenses Built With Very Small Circuits and LEDs Promises Bionic Eyesight", IEEE Spectrum.org/biomedical/bionics, downloaded Jul. 10, 2012.

European Search Report for corresponding Application No. 13152733.5-1562 dated Apr. 30, 2013.

Singapore Search Report for corresponding Application No. SG-201300387-6 dated Apr. 7, 2013.

* cited by examiner

OPHTHALMIC LENS ASSEMBLY HAVING AN INTEGRATED ANTENNA STRUCTURE

BACKGROUND OF THE INVENTION

1. Field of the Invention

The present invention is directed to optical lenses, and more particularly to optical lenses, such as wearable lenses, including contact lenses, implantable lenses, including intraocular lenses (IOLs) and any other type of device comprising an optical component that incorporates electronic circuits and associated antennas/antenna assemblies for information reception, information transmission and/or charging/energy harvesting.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the precorneal (tear) film. The use of embedded electronics in a lens assembly introduces a potential requirement for communication with the electronics and for a method of powering and/or re-energizing the electronics.

Often it is desirable to provide for communication to or from the embedded electronics for the purpose of control and/or data gathering. Communication of this nature should preferably be performed without direct physical connection to the lens electronics, such that the electronics may be fully sealed and to facilitate communication while the lens is in use. Hence it is desirable to couple signals to the lens electronics wirelessly using electromagnetic waves. Accordingly, there exists a need for an antenna structure appropriate for use in an optical lens assembly such as a contact lens.

The electronics in these applications often may require a power source. Accordingly, it may be desirable to incorporate a self-contained power storage device such as a rechargeable battery or capacitor. Alternately, the electronics may be inductively powered from a distance rather than being powered from a self-contained power storage device, and thus there is no need for recharging. An acceptable method for recharging a battery is through inductive coupling, whereby an external coil is magnetically coupled to a coil that is coupled to, connected to or otherwise associated with a charging circuit adapted to recharge the battery imbedded in the device. Accordingly, there exists a need for inductive structures, for example, antennas, antenna assemblies and/or coils appropriate for use in an optical lens assembly. Further, it is desirable to provide a convenient method for aligning the coil structure with an external inductive coil structure for efficient near-field coupling.

Embedding electronics and communication capability in a contact lens presents general challenges in a number of areas, including the limited size of the components, in particular the thickness as well as the maximum length and width, the limited energy storage capacity in batteries or super capacitors, the limited peak current consumption due to higher battery internal resistance in small batteries and limited charge storage in small capacitors, the limited average power consumption due to limited energy storage and the limited robustness and manufacturability of small and especially thin components. With respect to communication devices, specific challenges include limited antenna efficiency, which is directly related to size or area and for a loop antenna, the number of turns, and antenna efficiency. In addition, there is also a limited set of frequency bands allocated by regulatory bodies for these applications, the choice of which affects the efficiency of a given structure, the maximum allowable transmitter power, potential interference, and other aspects of the communication link. Further characteristics of on-body propagation and absorption depend on frequency, along with accepted safe limits for absorption of electromagnetic energy. Various government agencies may or may not issue guidelines or regulations relating thereto. Antenna efficiency on-body is degraded for predominantly electric-field or "E-field" antennas. Similarly, for wireless charging of the battery or similar device, the size of the antenna relates to the maximum inductance achievable and the maximum voltage or current that may be transferred to the device.

Accordingly, there exists a need for providing a mechanically robust antenna assembly that meets the requirements for functionality and performance in the volume and area of a contact lens.

SUMMARY OF THE INVENTION

The antennas and/or antenna assemblies of the present invention overcome the disadvantages as briefly set forth above.

In accordance with a first aspect, the present invention is directed to an ophthalmic lens assembly. The ophthalmic lens assembly comprising a lens configured for placement in at least one of the inside and proximate to a surface of an eye, the lens including an optic zone configurable for at least one of vision correction and vision enhancement, and one or more electronic components for enabling the vision correction and vision enhancement, and at least one antenna arrangement operatively associated with the one or more electronic components for providing at least one of one or two way communication with the one or more electronic components and power transfer.

In accordance with another aspect, the present invention is directed to a lens assembly. The lens assembly comprising a lens, including an optic zone for at least one of image enhancement, image capture and vision correction, and one or more electronic components for enabling image enhancement, image capture and vision correction, and at least one antenna arrangement operatively associated with the one or more electronic components for providing at least one of one or two way communication with the one or more electronic components and power transfer.

In accordance with yet another aspct, the present invention is directed to a lens assembly. The lens assembly comprising a lens, including an optic zone for at least one of image enhancement, image capture and vision correction, and at least one antenna arrangement operative associated with the lens, wherein energization and de-energization of the at least one antenna arrangement causes a mechanical change in the lens.

In accordance with the present invention, an antenna or antenna assembly may be incorporated into mechanical devices such as ophthalmic devices, including lenses and contact lenses. While exemplary embodiments will be described with respect to contact lenses (wearable) or implantable lenses (IOLs), it is important to note that the present invention may be utilized in any number of related or non-related devices. Wearable or contact lenses may incorporate a lens assembly having electronically adjustable focus to augment the performance of the eye and/or it may incorporate electronic sensors to detect concentrations of particular chemicals in the tear film. The use of such embedded electronics in a lens assembly potentially introduces the need for one and/or two way communication, and for a method of powering the electronics or recharging a power storage device. The antenna/antenna assembly of the present invention may be utilized to transmit and/or receive information and/or data as well as provide a means for charging the battery, batteries or capacitors utilized to power the electronics by inductive charging or radio frequency (RF) energy harvesting methods. As known in the relevant art, RF energy harvesting systems may be implemented where circuit operation is similar to inductive charging, but at higher frequencies, for example, 900 megahertz to 2.4 gigahertz. In the art, "inductive charging" is often associated with low frequency, for example, 125 kilohertz or 13.5 megahertz, near field coupling to a coil-like structure and RF energy harvesting is associated with longer distance, lower power, higher frequency waves coupled to an RF antenna.

An exemplary optical lens assembly in accordance with the present invention may comprise a circuit board or substrate, an electronic circuit, a lens structure (optics) and an antenna structure. The electronic circuit may comprise a number of electronic components mounted on the circuit board and the circuit board may provide wiring traces to interconnect the electronic components. The circuit board may be mechanically attached to the lens to form a rigid component of the optical lens assembly. Alternately, the circuit board may not be mechanically attached to the lens and thus not form a rigid component of the optical lens assembly. This arrangement may vary depending on the type of lens. In some exemplary embodiments, the antenna structure or antenna may include a coil comprising one or more loops of wire mounted around and concentric with the lens structure. In alternate exemplary embodiments, the antenna may comprise one or more wiring traces on the circuit board. The antenna may be electronically coupled to the electronic circuit. In some exemplary embodiments, the electronic circuit may provide a transmittal signal to the antenna in order to transmit an outgoing electromagnetic signal board on the transmit signal while in alternate exemplary embodiments, the antenna may receive incoming electromagnetic signal and provide a received signal to the electronic circuit. In yet another alternate exemplary embodiment, the antenna may be utilized to transmit and receive signals. In yet another alternate exemplary embodiment, the antenna may be utilized to inductively charge a storage element or battery. In some exemplary embodiments, a single antenna may also be utilized for both communication and power transfer as is described in detail subsequently.

Antennas and antenna systems or assemblies incorporated into medical devices such as ophthalmic devices may be utilized or configured for a wide variety of applications. Applications include transmitting/receiving data to/from the ophthalmic device, sensing information from the environment in which the ophthalmic device is placed, charging batteries associated with the ophthalmic device and actuation or activation of other devices. Data flow to and from the ophthalmic device may include communication with key fobs, smart phones or other hand-held devices and wireless networks, cases for holding the ophthalmic devices, e.g. cleaning cases for contact lenses that utilize chemical or UV based disinfection systems, as well as any other types of devices capable of receiving text information, video information, telemetry information, graphics, software or code for reprogramming or updating, and the like via an RF or inductive wireless link. The data or information to be transmitted or received may include tear film analysis, intra ocular pressure, heart rate, blood pressure and the like. The ophthalmic device may be utilized to sense any number of parameters depending on the device application, for example, ciliary muscle contraction for an accommodating lens. Relatedly the output from the antenna or antenna system may be utilized to actuate or activate secondary devices for changing the optics of the device and to dispense drugs or therapeutic agents. The antennas and antenna assemblies may be utilized, as stated above, to recharge batteries or for continuous powering from a remote source. This may be in the form of inductive powering rather than charging. The antennas may also be utilized to communicate between ophthalmic devices, such as lenses, to detect eye convergence during reading or to synchronize behavior for three-dimensional holographic realization.

The antennas and antenna assemblies may be physically realized in any number of ways. Physical realizations include conductive traces on a circuit incorporated in an ophthalmic device, and/or turns of wire embedded in the device, conductive traces printed in/on the device, and/or as a layer in a stacked die assembly. For example, an antenna may be fabricated on a circular/washer or arc shaped layer, with traces on one or both sides of the layer, on substrate materials with the appropriate trace metallurgy. Multiple antennas on a single device may be utilized as well.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1A:
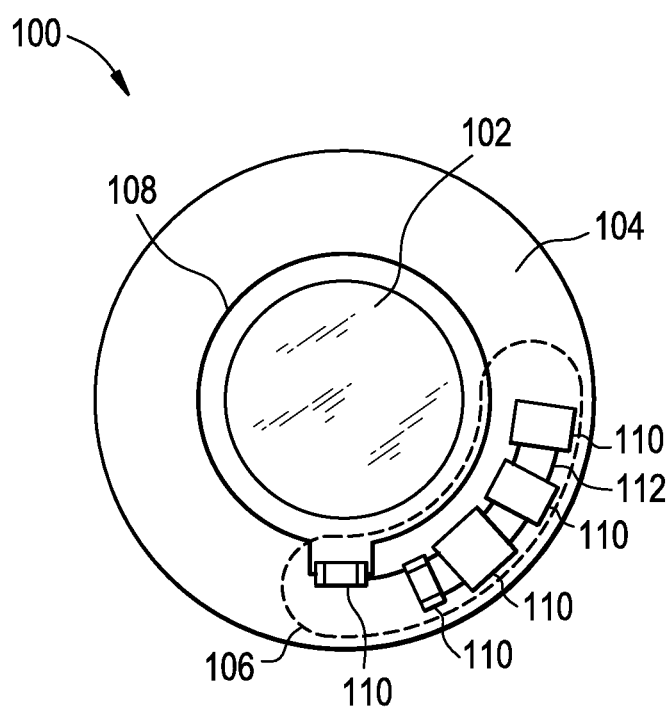
FIG. 1A is a diagrammatic representation of a first exemplary embodiment of an optical lens assembly comprising a single loop antenna in accordance with the present invention.

Referring to FIG. 1A there is illustrated a first exemplary embodiment of an optical lens assembly 100. Although illustrated as a contact lens, it is important to note that the present invention may be utilized in conjunction with any number of devices having medical and ophthalmic applications as well as any devices incorporating lenses, such as cameras, binoculars and microscopes. The exemplary optical lens assembly 100 comprises a lens structure 102, a circuit board 104, an electronic circuit 106 positioned on the circuit board 104, and a single turn loop antenna 108 also positioned on the circuit board 104 so as not to interfere with the lens structure 102. As utilized herein, the lens structure 102 may include a portion of an assembly that acts as an optical lens and not necessarily a separate component, but rather a region of a component such as a hydrogel overmolding. The electronic circuit 106 and the antenna 108 may be connected to or mounted to the circuit board 104 by any suitable means, for example, solder, wire-bond, conductive epoxy, conductive ink and conductive polymer and in any suitable configuration for any number of applications. The circuit board 104 as used herein may include any suitable substrate, including copper traces on a flexible polyimide substrate with a nickel-gold surface finish. Circuit boards are described in more detail subsequently. The electronic circuit 106 may comprise one or more electronic components 110 mounted to the circuit board 104 and the circuit board 104 may comprise interconnect conductive traces 112 to interconnect the one or more electronic components 110. The circuit board 104 may be attached to the lens structure 102 by any suitable means. For example, the circuit board 104 may be mechanically connected to the lens structure 102 to form a rigid component of the optical lens assembly 100. The single-turn loop antenna 108 may be formed from any number of suitable conductive materials and constructed utilizing any number of techniques. In the illustrated exemplary embodiment, the antenna 108 may be formed by wiring traces on the circuit board 104 and arranged to form an electromagnetic structure having predetermined characteristics for operation as an antenna, such as directivity, efficiency and/or gain when worn in a body or in-eye, or as an inductor for magnetic coupling to another inductor. The single-turn loop antenna 108 may be electrically coupled to the electronic circuit 106 by wiring traces 112. As stated above, the antenna may be fabricated from any number of suitable conductive materials and alloys, including copper, silver, gold, nickel, indium tin oxide and platinum. Preferably, the antenna is fabricated from a non-reactive, biocompatible material.

Figure 1B:
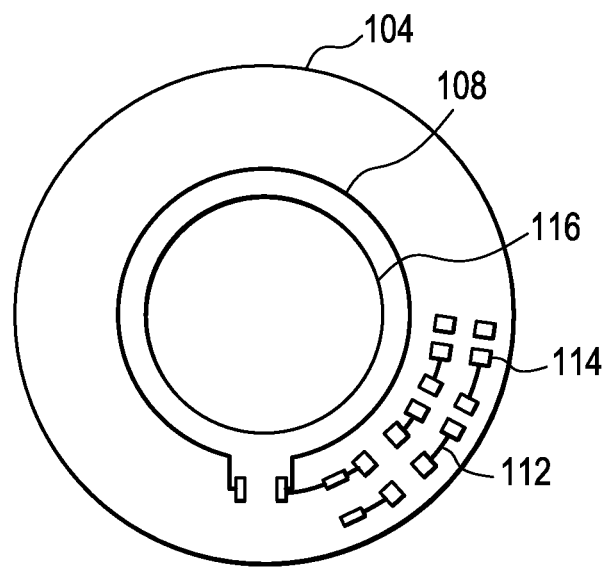
FIG. 1B is a diagrammatic representation of a first exemplary circuit board of the optical lens assembly of FIG. 1A.

FIG. 1B illustrates additional details of the circuit board 104 of the exemplary optical lens assembly 100 of FIG. 1A. The circuit board 104 may comprise mounting pads 114 to facilitate electrical connection and mounting of the electronic components 110 (FIG. 1A). The mounting pads 114 may be constructed from any number of suitable materials, for example, the pads 114 may be constructed with the metal layer that forms the metal traces 112 and may also be covered or more appropriately, plated utilizing any suitable process, with additional metal layers to improve manufacturability and reliability as is known to one of ordinary skill in the art. The circuit board 104 may also be constructed to provide an opening 116 in which a lens structure or optics section 102 may be mounted (FIG. 1A) or through which light may pass by a lens structure mounted on one side of the circuit board 104. The circuit board 104 may comprise conducting and insulating layers, for example, soldermask to cover the top conducting layer or insulators to separate conducting layers as is explained in greater detail subsequently. There are a wide variety of alternate configurations.

Figure 2:
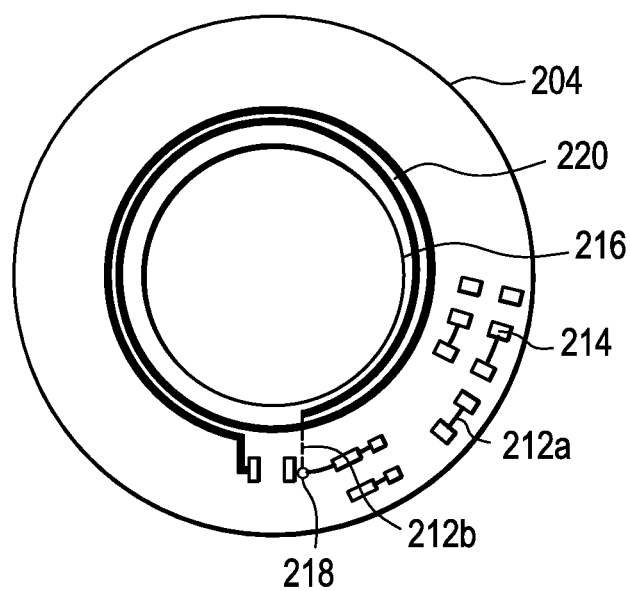
FIG. 2 is a diagrammatic representation of a second exemplary circuit board in accordance with the present invention.

FIG. 2 illustrates an alternate exemplary circuit board 204 that may be utilized with the optical lens assembly 100 illustrated in FIG. 1A. Circuit board 204 comprises both top side conductive interconnect traces 212a and bottom side conductive interconnected traces 212b (shown in phantom), through-holes or vias 218 for making electrical connections between the top and bottom sides, mounting pads 214, a center opening 216 and a multi-turn loop antenna 220 rather than a single turn loop antenna. The multi-turn loop antenna 220 comprises two or more turns of wire, conductive traces or the like formed in either or both of the top side or the bottom side of the circuit board 204. If multiple antennas are utilized on opposite sides, the through-hole or vias 208 may be utilized to make connections therebetween. It will be appreciated that the circuit board 204 may comprise additional metal layers and that any combination of layers may be used to construct the multi-turn loop antenna 220.

Figure 3:
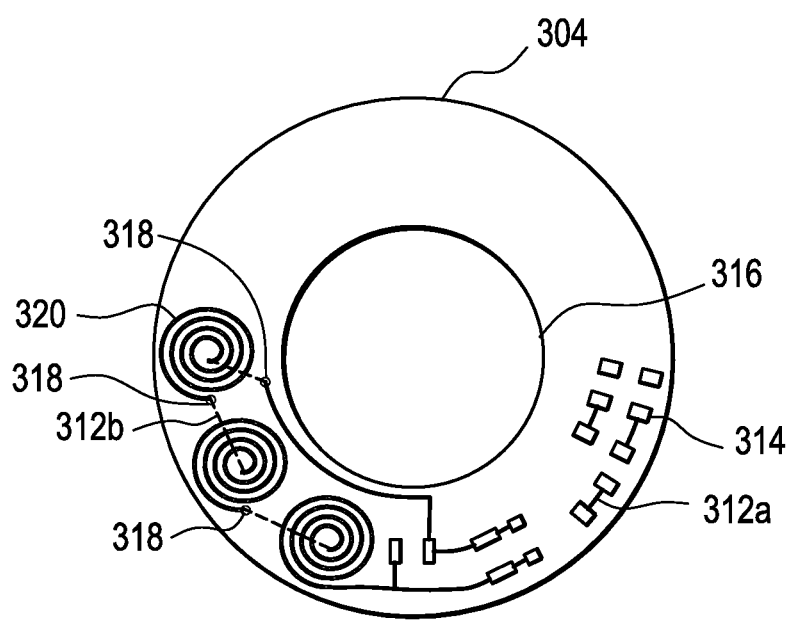
FIG. 3 is a diagrammatic representation of a third exemplary circuit board in accordance with the present invention.

Referring now to FIG. 3, there is illustrated yet another alternate exemplary circuit board 304 that may be utilized with the optical lens assembly 100 illustrated in FIG. 1A. The circuit board 304 comprises top side conductive interconnect traces 312a, bottom side conductive interconnect traces 312b, (illustrated in phantom) through-hole vias 318, mounting pads 314, a center opening 316 and one or more spiral antenna structures 320. The one or more spiral antenna structures 320 each comprise one or more turns of wire, conductive traces or the like formed in either the top side metal, the bottom side metal or both the top side and bottom side metal of the circuit board 304. If one or more antenna structures 320 are utilized on opposite sides, the through-hole vias 318 may be utilized to make connections therebetween. It will be appreciated that the circuit board 304 may comprise additional metal layers and that any combination of layers may be utilized to construct the spiral antenna structures 320. The antenna structures alternately may be embedded on an inner conducting layer, with other conducting layers above and/or below the antenna structures 320.

Figure 4:
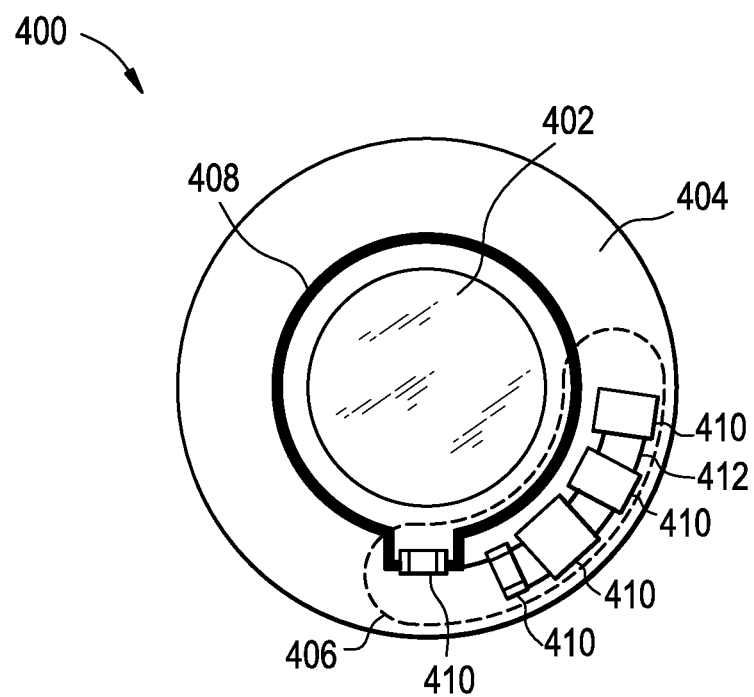
FIG. 4 is a diagrammatic representation of a second exemplary embodiment of an optical lens assembly comprising a coil antenna subassembly in accordance with the present invention.

FIG. 4 illustrates another exemplary embodiment of an optical lens assembly 400. The optical lens assembly 400 comprises a lens structure or optics 402, a circuit board 404, an electronic circuit 406 and a coil antenna subassembly 408. The electronic circuit 406 may comprise electronic components 410 mounted on the circuit board 404 and the circuit board 404 may provide conductive interconnect traces 412 to interconnect the electronic components 410. As in the previously described exemplary embodiments, the electronic components may be connected to the circuit board 404 by any suitable manner, including mounting pads (not illustrated). The circuit board 404 may be attached to the lens structure 402 by any suitable means. For example, the circuit board 404 may be mechanically connected to the lens structure 402 to form a rigid component of the optical lens assembly 400. The coil antenna subassembly 408 may comprise one or more turns of wire or the like on a circular form to create an electromagnetic structure having desirable characteristics for operation as an antenna, such as directivity, efficiency or gain when worn on a body or in eye, or as an inductor for magnetic coupling to another inductor coil. The coil antenna subassembly 408 may be electrically coupled to the electronic circuit 406 by the wiring traces 412 and the electronic components 410. The notable or primary difference between the optical lens assembly of FIG. 1A and the optical lens assembly of FIG. 4 lies in the antenna. The device of FIG. 1A comprises a single-turn loop antenna 108 constructed with the circuit board 104 whereas the device of FIG. 4 comprises a coil antenna subassembly 408 separate from the circuit board 404. This design may provide benefits for fabrication, cost, assembly, antenna performance, as well as other characteristics. The antenna subassembly 408 may be integrated with the lens 402, for example, as a wire or printed coils within the lens component.

It is important to note that the circuit boards described herein may be constructed from any number of biocompatible materials or combination of materials utilizing any number of fabrication techniques. A more detailed description is given subsequently.

Figure 11:
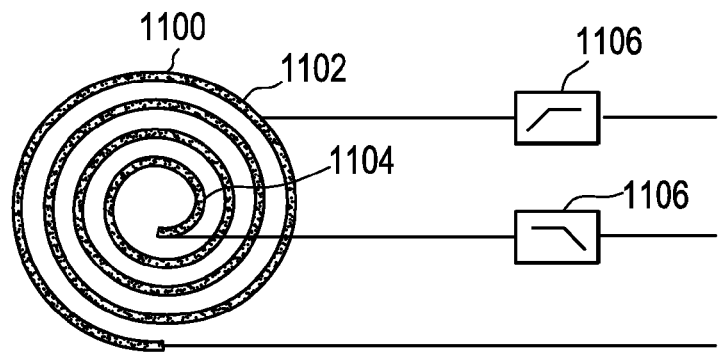
FIG. 11 is a diagrammatic representation of a four turn spiral antenna that may be utilized for both communication and power transfer in accordance with the present invention.

Referring to FIG. 11, there is illustrated an exemplary embodiment of a single antenna 1100 that may be utilized for one or both communication and power transfer. In FIG. 11, the single antenna 1100 is configured as a single four loop spiral antenna with a first tap point 1102 after the first loop and a second tap point 1104 after the fourth loop. The single loop tap 1102 is intended, for example, for 900 megahertz while the four loop tap 1104 is intended for 13.5 megahertz. A high pass filter 1106 is coupled to the first tap point 1102 while a low pass filter 1108 is coupled to the second tap point 1104. The high pass filter 1106 may couple an electrical signal to an RF transmit or receive circuit such as for communication or power coupling. The low pass filter 1108 may also couple an electrical signal to a lower frequency transmit or receive circuit such as for communication or power coupling. Low and high pass filters may be implemented in a wide variety of configurations using a wide variety of components and/or software as is known to one skilled in the relevant art.

As is known in the relevant art, printed circuit boards are commonly manufactured or fabricated with one or more layers of fiberglass reinforced epoxy laminate sheets such as FR-4 fiberglass epoxy or a polyimide flexible material to produce a flexible circuit board. Conductive circuit traces may be created by coating an insulating layer with a predetermined thickness of copper or other suitable conductive material, applying a photoresistive material thereon, and selectively patterning and etching the material based on a desired circuit routing pattern. Multiplayer boards may be built up in layers with adhesive. The upper traces may then be plated with nickel-gold or other materials to achieve suitable corrosion resistance, solderability and bondability.

Antenna traces may be created directly within the contact lens or an optic insert. The lens molding process may allow for insertion of an antenna or deposition of an antenna within the polymer of the contact lens. An antenna may be deposited as a printed, curable trace during manufacture. An insert, containing the antenna, may be added to the contact lens during molding. An antenna may be fabricated on an optic insert by selectively depositing metal, broadly depositing then selectively removing metal, depositing a liquid curable conductor, or other means. The functionality of the antenna is similar to what has been described for a circuit board; however, the physical realization is on a polymer or plastic instead of typical circuit board materials.

A coil subassembly may be manufactured by winding enamel coated wire on a cylindrical form that is incorporated as part of a lens assembly. Alternately, wire may be wound onto an outer part of the lens structure itself and optionally bonded (glued) or otherwise attached to the lens structure. Any suitable means for attaching the wire to the lens, for example, small tabs may be utilized to secure the windings in position. In yet another alternate embodiment, a coil may be created by selectively etching, for example with a laser or mechanical means, a spiral or circular pattern of conductive traces in a conductive layer on an outer or inner portion of the lens assembly.

An antenna may also be realized in a contact lens by first fabricating a stacked die structure which is then embedded within the contact lens. An antenna may be fabricated on a circular/washer or arc-shaped layer, with conductive traces on one or both sides of the layer, on substrate materials like glass, silicon or alumina, with the appropriate trace metallurgy. An antenna layer may be combined with other layers to form an electronic system, potentially including batteries, sensors and any number of other electronic circuits or devices. The antennas may be configured as full loops or partial loops on opposite sides of a device or bypassing other devices, and all be interconnected through vias and/or bridges.

Figure 12:
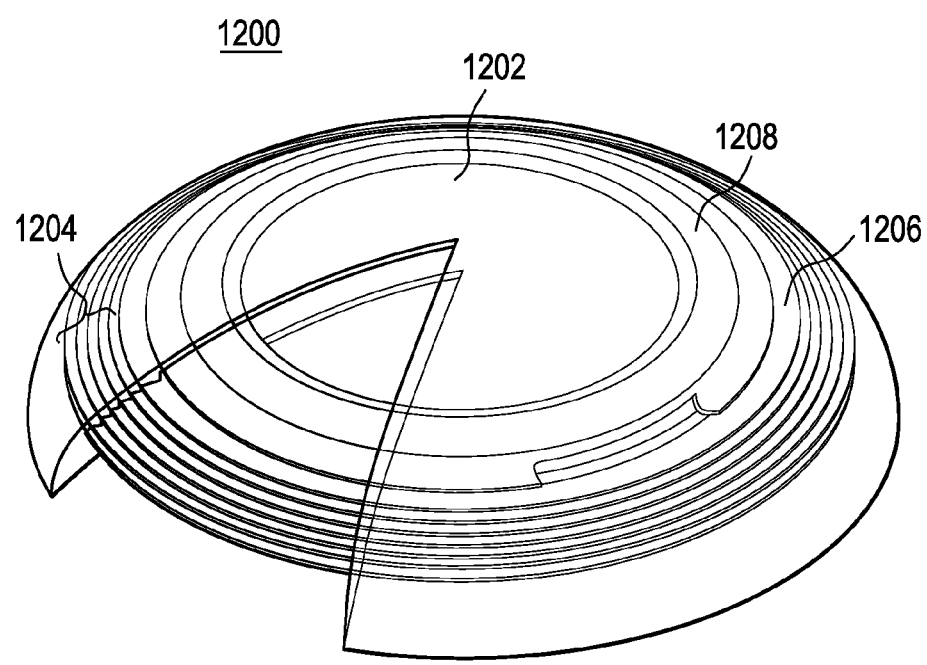
FIG. 12 is a diagrammatic representation of a die stack configuration in accordance with the present invention.

FIG. 12 illustrates an exemplary stacked die arrangement incorporated into a contact lens 1200. As illustrated, the contact lens comprises an optic lens zone 1202, one or more layers of electronic components 1204, and at least one antenna layer 1206. The optic lens zone 1202 comprises a front optic, a rear optic and a metalized flange 1208 on the perimeter thereof. The stacked die is encapsulated into the polymer forming the lens 1200. It is important to note that any of the antennas described herein, including the single-turn loop antenna, the multi-loop antenna, the spiral antenna or the coil antenna subassembly may also be encapsulated into the polymer forming the lens with or without a substrate.

Regardless of the physical implementation of the conductive antenna traces, for example, a wire coil configuration, on a circuit board, via a stacked die or conductive traces printed directly on and/or in the material forming the lens, the antenna traces should preferably be insulated from the surrounding conductive fluids found in or on the eye. The eye's tear film is composed of three layers. The first or bottom layer is the layer that coats the eye and comprises mucin which is created by cells in the conjunctiva referred to as goblet cells. The mucin fills in microscopic irregularities on or in the eye's surface which is important to clear vision. The second layer or middle layer of the tear film comprises a watery substance that makes up the bulk of the tear film. A majority of the watery component is produced or supplied from the main lacrimal or tear gland. The third or top layer of the tear film comprises a thin layer of oil secreted by the meibomian glands and functions to prevent the tears from evaporating too quickly. The aqueous humor is a clear waterlike fluid within the anterior chamber between the cornea and the crystalline lens of the eye which is similar to blood plasma in composition. The vitreous humor is a jellylike fluid in the posterior chamber between the crystalline lens and the retina of the eye. Both tears and aqueous humor may contain conductive components. Accordingly, without proper insulation, undesirable shorts could develop between antenna traces, or the performance of the antenna may be degraded by the presence of a nearby conductive fluid or material with a high dielectric constant. For example, a tear film, as stated above comprises a conductive solution of water and salt ions. Human tissue as well as tear film also exhibit dielectric properties which could change the tuning, frequency response and efficiency of the antenna.

Figure 13:
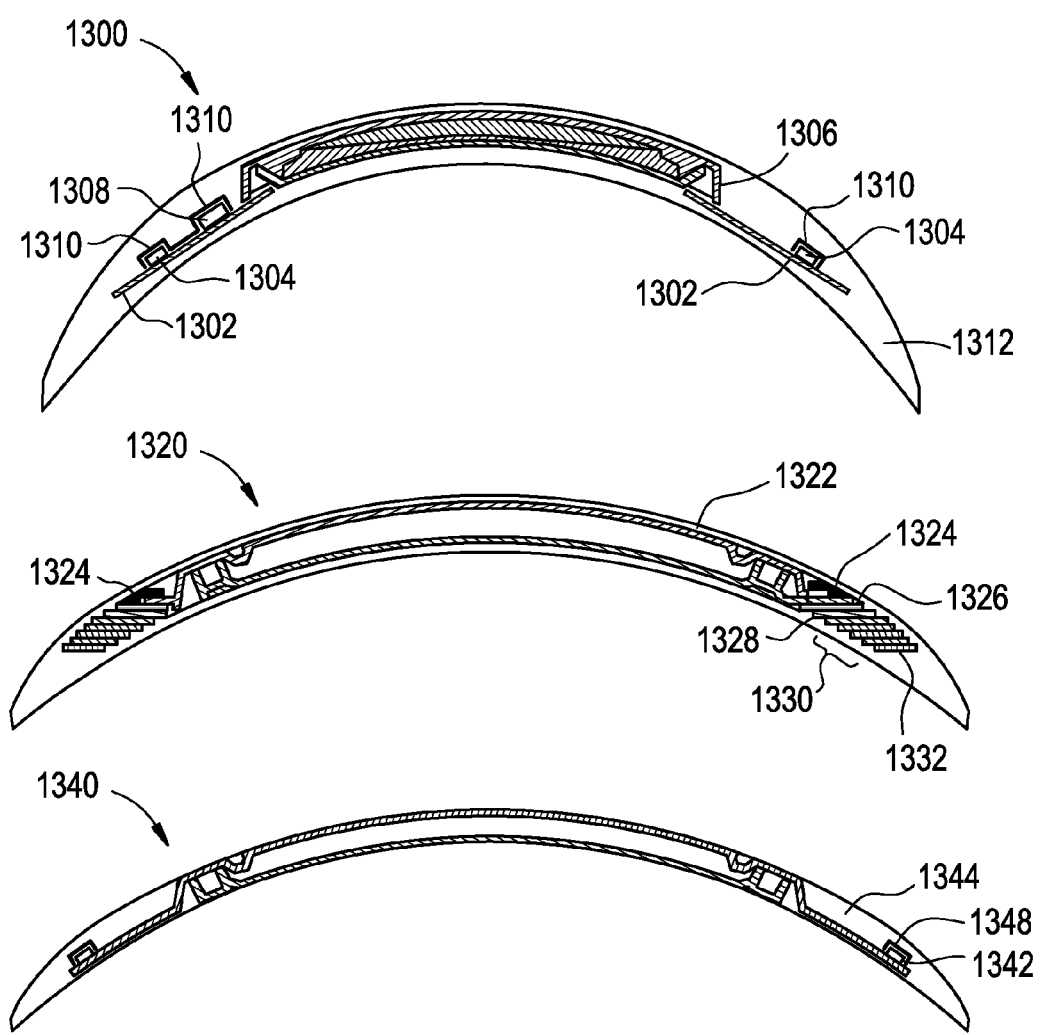
FIG. 13 is a diagrammatic representation of the cross sections of designs implementing antennas in contact lenses with the antenna conductors insulated from the conductive tear film in accordance with the present invention.

Referring now to FIG. 13, there is illustrated, in cross-section, three exemplary embodiments of antenna configurations in lenses, for example, contact lenses. Lens 1300, as illustrated, comprises a flexible circuit board 1302 on which the antenna traces 1304 may be patterned. Also mounted to the circuit board 1302 is the lens module 1306 and electronic components 1308. An insulating layer 1310 is coated on the antenna traces. The contact lens polymer 1312 encapsulates the entire assembly. Lens 1320, as illustrated, comprises a stacked die arrangement 1322 with an antenna layer 1326 as the top layer. The stacked die arrangement 1322 also comprises a number of layers of electronic components 1328, 1330 and 1332 arranged in layers. Layer 1328 may comprise a number of functional components, for example, an integrated circuit RF receiver. Layer 1330 may comprise, for example, multiple battery layers or other energy storage devices. Layer 1332 may comprise additional circuitry or antennas. An insulating layer 1324 may be coated on top of the antenna layer 1326. Once again, contact lens polymer encapsulates the entire assembly. Lens 1340 as illustrated, comprises an antenna 1342 mounted directly on the polymer forming the lens 1344 with an insulating layer 1348 positioned thereon. An integrated circuit 1346 may be connected to the antenna 1342, for example, as an RF receiver. The contact lens polymer encapsulates the whole assembly.

The insulating layers 1310, 1324 and 1348 may be implanted in any number of ways. For example, on a circuit board, it is typical to implement a soldermask layer which insulates all traces except for defined pads which are left open to permit connection to components such as discrete components, battery and/or integrated circuits. In a die stack arrangement, underfill or other adhesives or encapsulants may be used as is standard practice in die attachment and packing. For a design utilizing antenna traces realized directly on the optic polymer, an insulating layer may be deposited through standard deposition or coating techniques known in the semi-conductor processing industry. Any of these approaches may undergo further insulating or encapsulation, including paralyne coating, dielectric deposition, dip coating, spin coating or painting. The insulating material must have sufficient dielectric strength in the presence of an applied electromagnetic field given the specific trace geometry and separation.

Figure 13A:
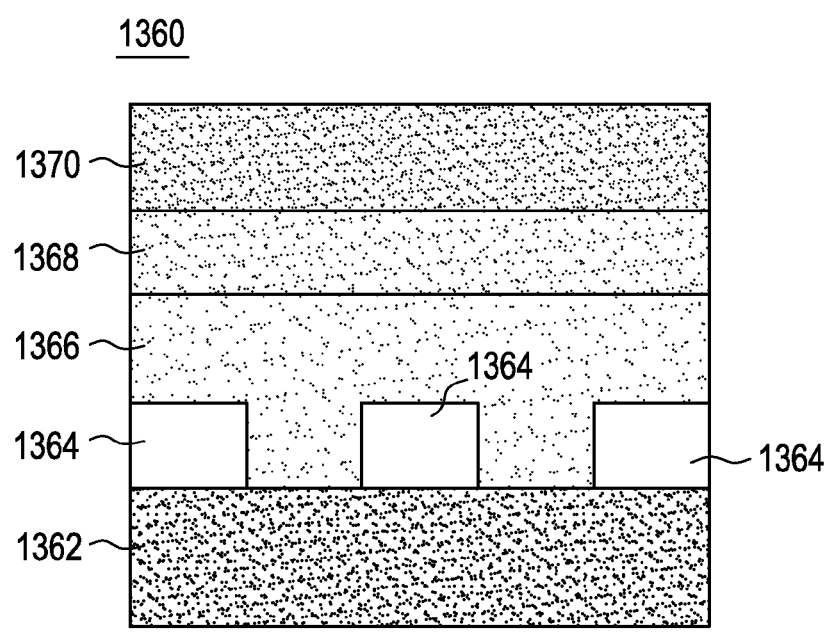
FIG. 13A is a cross-sectional view of antenna traces on a substrate with insulation in accordance with the present invention.

Referring now to FIG. 13A, there is illustrated, in cross-section, a contact lens 1360 having multiple components, including antenna traces on a substrate with insulation thereon. The substrate 1362 may comprise any suitable surface, including a circuit board, silicon or other material used in a die stack, optic plastic/polymer, or any other substrate material suitable for use with optic and metallic traces. The antenna traces 1364 may be formed on the substrate 1362 utilizing any suitable technique such as those described herein. For an antenna implemented as a wire assembly, the antenna may not be formed directly on the substrate. An insulating layer 1366 provides electrical and mechanical insulation between the antenna traces 1364 and also between the antenna traces 1364 and the surrounding environment, which may include a biocompatible polymer 1368 and the ocular environment 1370 which includes the tear film and the like which comes into contact with the lens 1360. The insulating layer 1366 and the biocompatible polymer layer 1368 may also provide chemical as well as mechanical insulation for the antenna traces 1364 and the substrate 1362.

The physical separation between the antenna and nearby substances with high permittivity or nearby objects connected to various circuit nodes can affect the antenna frequency response, tuning, and efficiency. Parasitic capacitance may be distributed around the loop antenna causing substantially altered performance from the design goal. Other circuit traces should be kept as far as possible from the antenna trace to avoid parasitic coupling. Electromagnetic field simulations should be performed to design the antenna in the presence of nearby objects and substances.

Figure 15:
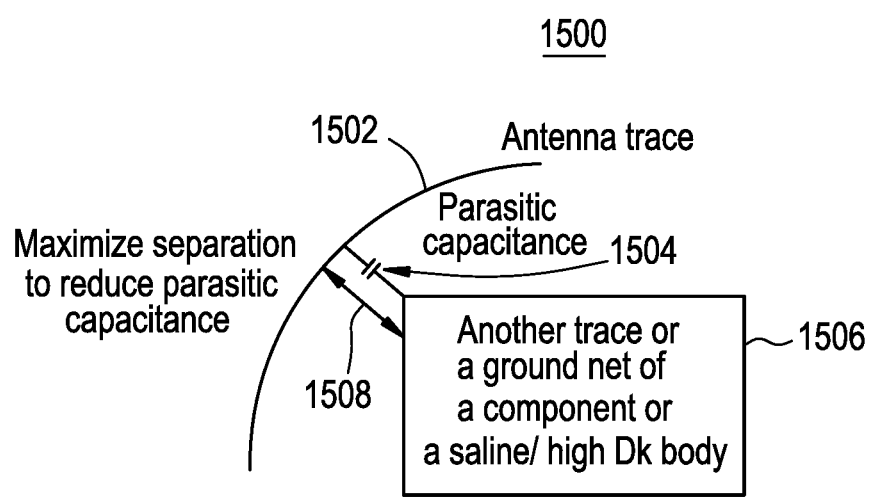
FIG. 15 is a diagrammatic representation of an antenna trace with parasitic coupling in accordance with the present invention.

Turning now to FIG. 15, there is illustrated a diagrammatic representation of antenna trace parasitic coupling. The antenna trace 1502 may be implemented on any suitable substrate 1500, which may include a circuit board or a die stack utilizing any suitable techniques such as those described herein. Other components 1506 mounted on the substrate 1500 and located proximate the antenna trace 1302 may couple to the antenna trace 1502 through parasitic capacitance represented by capacitor 1504. As previously described, as well as known in the art, this coupling may significantly impact antenna performance. However, this parasitic coupling may be reduced by increasing the separation 1508 between the antenna trace 1502 at the other components 1506 by distance or through shielding material.

Figure 16A:
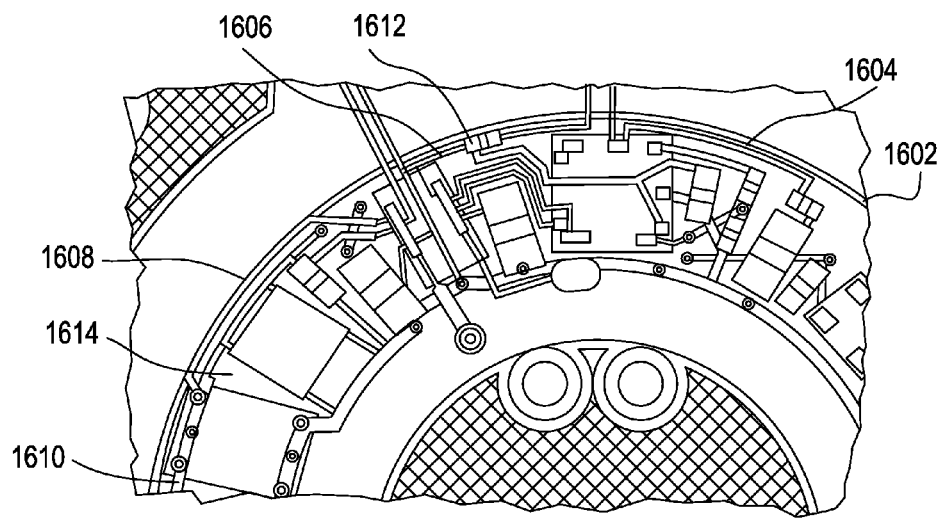
FIGS. 16 A and B are schematic representations of an antenna on a circuit board in accordance with the present invention.
Figure 16B:
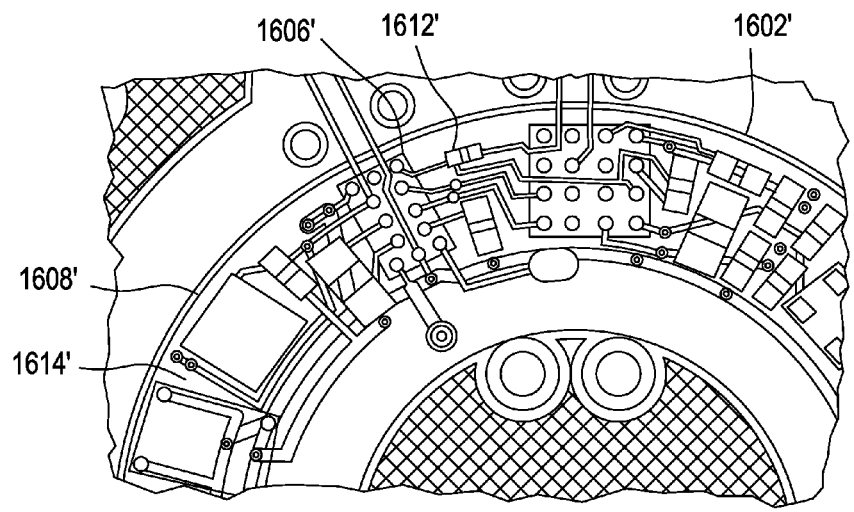

FIGS. 16A and 16B are schematic representations illustrating the concept set forth with respect to FIG. 15. In FIG. 16A, antenna trace 1602 on circuit board 1614 is close to traces 1604, 1606, 1608 and 1610 as well as electronic component 1612. Each of these conductive traces and/or electronic components may cause distributed parasitic capacitance along the antenna trace 1602. Accordingly, a single solution is illustrated in FIG. 16B, wherein the antenna trace 1602' on circuit board 1614' is separated from traces 1604', 1606', 1608' and 1610' as well as component 1614', thereby decreasing parasitic capacitance and improving antenna performance.

Antennas or antenna systems may serve as a means for receiving signals, as a means for transmitting signals, as an inductive coupling means, or any combination thereof. The function of an antenna determines its design as well as its supporting circuitry. For example, an antenna may be coupled to a receiver circuit, a transmitter circuit, an inductive coupling circuit or to any combination thereof. Basically, an antenna is an electrical device that converts electromagnetic waveforms into electrical signals, electrical signals into electromagnetic waveforms, or electrical signals into different electrical signals. The discussion below focuses on the three different uses of an antenna and its associated circuitry.

It is important to note that the circuits set forth and described subsequently may be implemented in a number of ways. In one exemplary embodiment, the circuits may be implemented using discrete analog components. In another exemplary embodiment, the circuits may be implemented in integrated circuits or a combination of integrated circuits and discrete components. In yet another alternate exemplary embodiment, the circuits or particular functions may be implemented via software running on a microprocessor or microcontroller.

Figure 5:
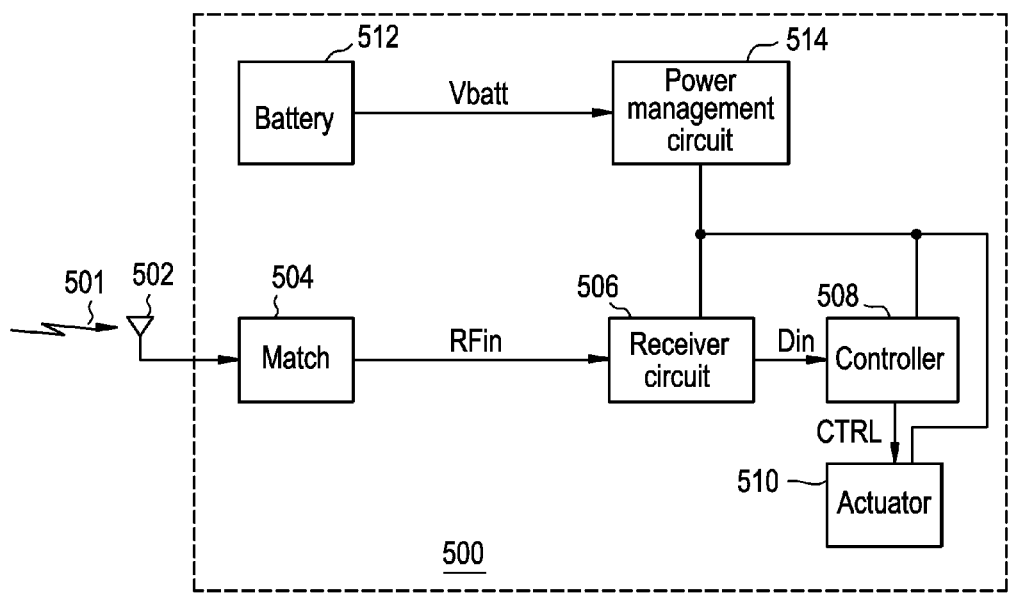
FIG. 5 is a block diagram representation of an antenna and receiver circuit in accordance with the present invention.

Referring to FIG. 5, there is illustrated an antenna 502 and associated radio receiver 500. The radio receiver electronic circuit 500 comprises an antenna match circuit 504, a receiver circuit 506, a controller 508, an actuator 510, a battery 512 and a power management circuit 514. In this configuration, the antenna 502 is adapted to receive an electromagnetic signal 501 and to provide a received electrical signal to the antenna match circuit 504. The antenna match circuit 504 may comprise any suitable circuitry necessary for balancing the impedance between the source and the load to maximize power transfer and/or minimize reflection from the load. Essentially, antenna impedance is the ratio of voltage to current at any point on the antenna and for efficient operation, the antenna impendence should be matched to the load, and thus a match circuit is utilized. In this instance, the match circuit 504 is adopted to provide an impedance match between the antenna 502 and the receiver circuit 506 for an optimum power match, noise match or other match condition as is known in the radio and circuit design arts. The receiver circuit 506 comprises any suitable circuitry necessary to process the modulated signal received by the antenna 502 and provide a demodulated signal to the controller 508. For purposes of clarity, modulation involves varying one or more properties of a signal or electromagnetic waveform. For example, a waveform may be amplitude modulated (AM), frequency modulated (FM) or phase modulated (PM). Other forms of analog as well as digital modulation exist. Demodulation, on the other hand, involves extracting the original information bearing signal from the modulated carrier wave. It is this demodulated information signal that provides instructions to the controller 508. The controller 508 in turn provides a control signal to the actuator 510 based upon the demodulated signal in order to control a state or operation of the actuator 510. The control signal may be further based on any internal state of the controller (for example, to implement control laws) and/or any other circuits coupled to the controller (for example, to implement a feedback control system or to modify the actuator operation based on other information, such as information based upon sensor data). The battery 512 provides a source of electrical energy for all components in the electronic circuit 500 requiring energy e.g. active components. The power management circuit 514 is adapted to receive a current from the battery 512 and condition it or regulate it to provide a workable output voltage suitable for use by the other active circuits in the electronic circuit 500. The controller 508 may also be utilized to control the receiver circuit 506 or other circuits in the receiver 500. The antenna 502 may comprise one or more of the configurations described herein. For example, a single-turn loop antenna, a multi-turn loop antenna, a spiral antenna, a coil antenna subassembly or a stacked-die configuration or arrangement.

As is known in the relevant art, the optimum transfer of power between an antenna and a receiving and/or transmitting circuit requires matching the impedance presented to the antenna and the impedance presented to the circuit. Essentially, optimum power transfer occurs when the reactive components of the antenna and circuit impedances are cancelled and the resistive components of the impedances are equal. A matching circuit may be introduced to couple the antenna to the circuit that meets the optimum power transfer criterion at each, thereby allowing for optimum power transfer to occur between the antenna and circuit. Alternately, a different criterion may be selected to optimize a different parameter such as maximum current or voltage at the circuit. Matching circuits are well known in the art and may be implemented with discrete circuit component such as capacitors, inductors and resistors, or with conductive structures, such as traces in a circuit board, that provide a desired impendence characteristic.

Impedances of small RF loop antennas are typically between 20 and 50 nanohenries, and matching component valves are in the range of 0.5 to 10 picofarads for capacitors and 3 to 50 nanohenries for inductors. Impedances of inductive charging coils are typically between 100 nanohenries and 5 nanohenries and associated capacitors for resonating the circuits are between 20 and 100 picoforads.

The actuator 510 may comprise any number of suitable devices. For example, the actuator 510 may comprise any type of electromechanical device, for example, a pump or transducer. The actuator may also comprise an electrical device, a chemical release device or any combination thereof. The actuator 510 may be replaced with a controlled device such as a light emitting diode or diode array or any other suitable display or user interface. In other words, the circuit 500 may utilize an actuator (action device) or a controlled device (passive device). As used in this context, a passive device is a device that does not output to or control another device, for example, actuators such as motors are active whereas displays or monitors are passive. In contrast, in electronics terminology, there are passive electronic devices such as resistors, capacitors and inductors and active devices such as transistors. Active devices as used in this context are devices capable of changing their "operational performance," such as transistors.

The battery 512 may comprise any suitable device for the storage of electrical energy. For example, the battery 512 may comprise a non-rechargeable electrochemical cell, a re-chargeable electrochemical cell, a storage electrochemical cell, and/or a capacitor. In alternate exemplary embodiments, no battery may be required as explained above with respect to RF energy harvesting or near field inductive coupling. Alternatively, mechanical vibration and similar means may be utilized to generate or harvest power.

The power management circuit 514 may comprise additional circuitry for a wide variety of functions in addition to regulating the output of the battery 512. For example, the power management circuit 514 may comprise circuitry for monitoring various battery parameters, such as charge, preventing overdischarge of the battery, and supervising the start up and shut down of the electronic circuit 500.

Figure 6:
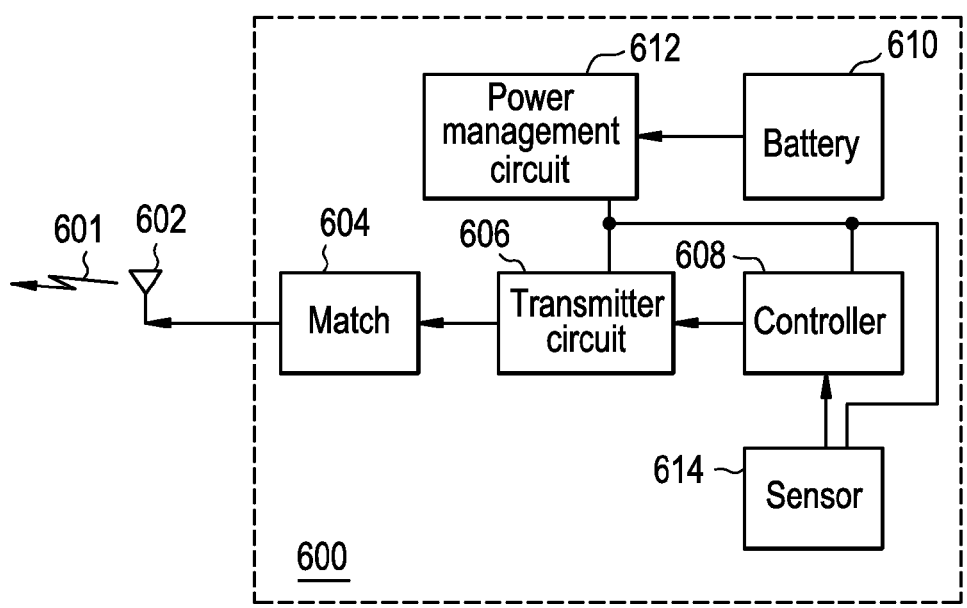
FIG. 6 is a block diagram representation of an antenna and transmitter circuit in accordance with the present invention.

Referring now to FIG. 6, there is illustrated an antenna 602 and associated radio transmitter or radio transmitter circuit 600. The radio transmitter electronic circuit 600 comprises an antenna match circuit 604, a transmitter circuit 606, a controller 608, a battery 610, a power management circuit 612 and a sensor 614. In this exemplary embodiment, the antenna 602 is adapted to receive a matched transmit electrical signal from the match circuit 604 and broadcast or radiate a transmit electromagnetic signal 601 based on the transmit electrical signal. Similarly to that described above, the match circuit 604 may be configured to provide an impedance match between the antenna 602 and the transmitter circuit 606 for an optimum power match, noise match or other match condition as is known to one of ordinary skill in the signal processing art. Rather than working in conjunction with an actuator, the controller 608 is coupled to and configured to receive a sensor data signal from the sensor 614. The sensor 614 may comprise any type of sensor, including mechanical sensors, chemical sensors, and/or electrical sensors. The controller 608 provides a transmit data signal to the transmitter circuit 606 based on the sensor data signal from the sensor 614. The transmit data signal may be further based on an internal state of the controller 608 and/or the state of the other circuits coupled to the controller 608. As before, the battery 610 provides a source of electrical potential energy for any of the components requiring energy (active components). Once again, the power management circuit 612 is configured to receive current from the battery 610 and to provide a regulated supply voltage to the other active components in the circuit 600. The antenna 602 may comprise one or more of the configurations described herein. For example, a single-turn loop antenna, a multi-turn loop antenna, a spiral antenna. a coil antenna subassembly or a stacked-die arrangement or configuration.

Figure 7:
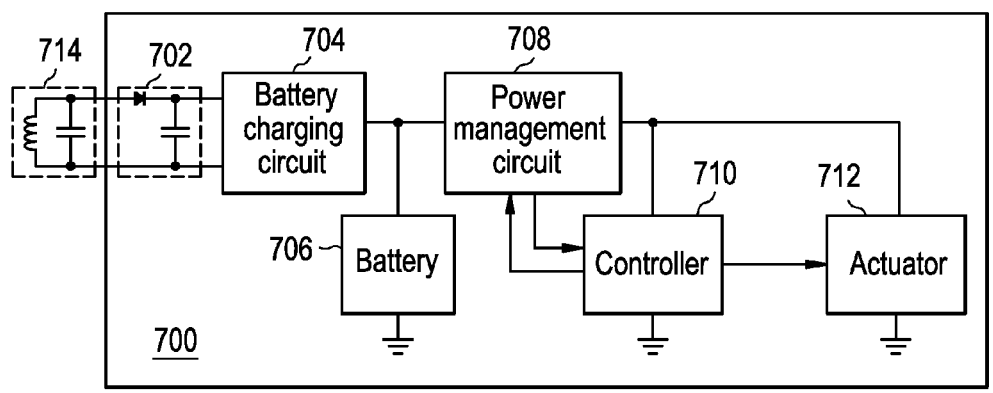
FIG. 7 is a block diagram representation of an inductive charging circuit in accordance with the present invention.

FIG. 7 illustrates an electronic circuit 700 comprising an inductive charging receiver. The electronic circuit 700 comprises a rectifier circuit 702, a battery charging circuit 704, a battery 706, a power management circuit 708, a controller 710 and an actuator 712. A secondary inductive circuit 714 is coupled to and provides a power signal to the rectifier circuit 702. The secondary inductive circuit 714 is essentially an inductive circuit in which the current is produced by a magnetic field from a primary circuit (not shown). In the simplest terms, a rectifier circuit converts an alternating current to a direct current. The rectifier circuit 702 is illustrated in its simplest form, essentially using a diode to allow current to flow in a single direction. The inductive circuit 714 is also shown in its simplest form with a coil in which current is utilized to create a magnetic field. Both of these circuits may be much more complex depending on what is needed for the particular application. Those skilled in the art will recognize many alternate exemplary embodiments of resonant circuits and rectifier circuits, including full wave bridge rectifiers which may or may not be coupled to inductors having a secondary tap that may improve the efficiency of the rectification, but essentially perform the same or similar function. The rectifier circuit 702 rectifies the power signal to provide a direct current (DC) signal to the battery charging circuit 704. The battery charging circuit 704 is coupled to the battery 706 which is also coupled to and provides energy to the power management circuit 708. It is important to note that while the figure illustrates an explicit connection at a single node coupling the battery charging circuit, the battery and the power management circuit, there are a wide variety of implementations with separate "managed power paths" with switches and switching networks to selectively couple the one or more devices. The power management circuit 708 may provide a regulated voltage supply to the controller 710 and actuator 712. The controller 710 may be further configured to receive an indicator signal from the power management circuit 708 and to provide control signals to the power management circuit 708. The controller 710 provides an actuator control signal to the actuator 712. In operation, the battery charging circuit 704 may sense the battery voltage of the battery 706 and the available voltage from the rectifier circuit 702. If the available voltage is greater than the battery voltage and if the battery voltage is below a desired charged level, then the battery charging circuit 704 may charge the battery until either the available voltage is too low or the battery voltage reaches the desired charged level. The controller 710 may operate under the control of an internal state machine or microprocessor core and software to periodically enter a low or high power state, and to command the power management circuit 708 to change an operating mode and to control the actuator 710. The power management circuit 708 may sense the battery voltage and provide an indication of the state of charge of the battery 706 on the indicator signal. The operation of the controller 710 may depend on the indicator signal and therefore the state of charge of the battery 706. The secondary inductive circuit 714 may comprise one or more of a single-turn loop antenna, a multi-turn loop antenna, spiral antenna structures, or a coil antenna subassembly.

Figure 8:
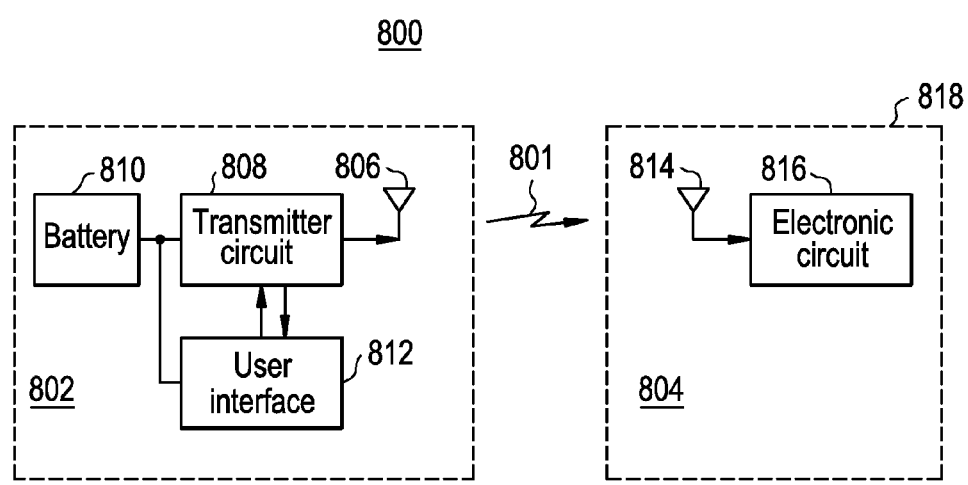
FIG. 8 is a block diagram representation of a transmitter circuit in combination with an optical lens assembly comprising an antenna and receiver in accordance with the present invention.

Referring now to FIG. 8, there is illustrated an exemplary transmitter and an exemplary optical lens assembly comprising a receiver as illustrated in FIG. 5. As illustrated, the overall system 800 comprises a control transmitter 802 and an optical lens assembly 804. The control transmitter 802 may comprise an antenna 806, a transmitter circuit 808, a battery 810 and a user interface 812. For example, the user interface 812 may be an optional component. The antenna 806 may comprise any suitable device such as those disclosed herein. It is important to note that the battery 810 may comprise any suitable device, including rechargeable batteries, non-rechargeable batteries, one or more capacitors and a power supply that works with an AC adapter as described above. The user interface 812 is coupled to the transmitter circuit 808 and may provide buttons or similar means for a user to control and/or observe the status of the transmitter circuit 808. In other words, the user interface 812 may comprise any suitable means through which a user or operator may command and communicate with the transmitter circuit 808 such as buttons, touch screen displays or any other known means. The transmitter circuit 808 generates and provides and electrical transmit signal to the antenna 801 in order to broadcast a transmit electromagnetic signal 801. The transmit electromagnetic signal 801 may be based on control information provided by the user/operator and/or may be based on an internal state of the transmitter 802. The optical lens assembly 804 may also comprise an antenna 814, an electronic circuit 816, which may be substantially similar to the circuit 500 of FIG. 5, and a lens structure 818 with which the antenna 814 and the electronic circuit 816 are incorporated.

Figure 9:
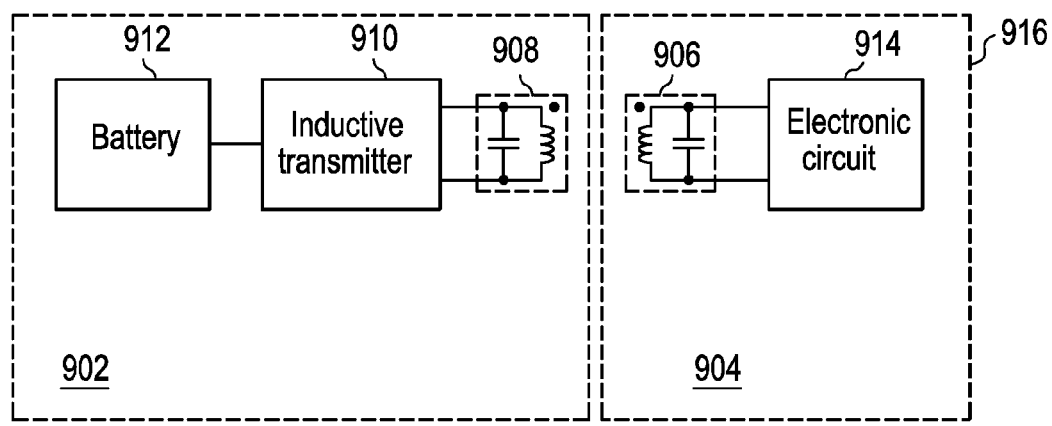
FIG. 9 is a block diagram representation of a primary inductive circuit in combination with a secondary inductive circuit incorporated into an optical lens assembly in accordance with the present invention.

Whereas FIG. 8 illustrates an exemplary transmitter and an exemplary optical lens assembly, FIG. 9 illustrates an exemplary inductive charging system 902 and an exemplary optical lens assembly 904, including a secondary inductive circuit 906 and an electronic circuit 914. The inductive charging system 902 comprises a primary inductive circuit 908, an inductive transmitter circuit 910 and a battery 912. The battery 912 provides a source of electrical potential energy to the inductive transmitter circuit 910. The inductive transmitter circuit 910 generates and provides a drive signal to the primary inductive circuit 908 in order to generate an alternating magnetic field in the primary circuit 908. The primary inductive circuit 908 may comprise any suitable design, for example, with either series or parallel circuit arrangements as is well known in the relevant art. The optical lens assembly 904 comprises a secondary circuit 906 and an electronic circuit 914. During the charging operation, the secondary circuit 906 may be magnetically coupled to the primary circuit 908 such that the induced magnetic field induces a current in the secondary circuit 906 which is provided to the electronic circuit 914. The electronic circuit 914 may comprise a circuit substantially similar to circuit 700 (FIG. 7) and the secondary circuit 906 may comprise any type of antenna such as those discussed herein. The electronic circuit 914 and the secondary circuit 901 may be incorporated into an optical lens assembly 916 in any suitable manner such as any of the exemplary embodiments described herein.

Figure 10:
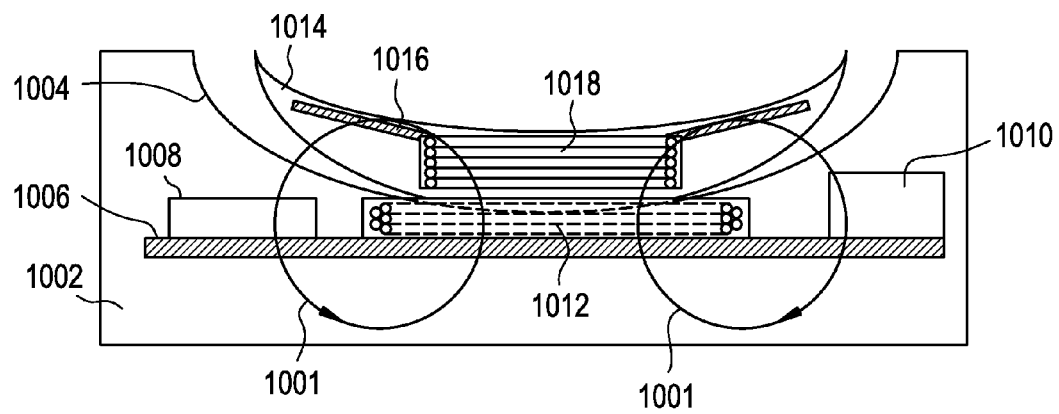
FIG. 10 is a block diagram representation of a contact lens inductive charging system incorporated into a contact lens holding case in accordance with the present invention.

The charging system illustrated in FIG. 9 may be incorporated into any number of suitable devices. FIG. 10 illustrates an exemplary contact lens case 1002 incorporating a charging system. The exemplary contact lens case 1002 comprises lens holder 1004, a circuit board 1006, an inductive transmitter circuit 1008, a power-source 1010, and a primary inductive antenna structure 1012. A contract lens 1014 comprises a circuit board 1016 and a secondary inductive antenna structure 1018. The lens 1014 is illustrated in profile and thus the optical structure is not shown. In operation, a user simply places the lens 1014 into the lens holder 1004. The lens holder 1004 is shaped in a manner to optimally align and achieve a desired amount of magnetic coupling between the secondary inductive antenna structure 1018 with the primary inductive antenna structure 1012 an indicated by magnetic field lines 1001.

Typically, for wireless communication, there is a range of frequencies, around 900 megahertz and 2.4 gigahertz where power levels allowed by regulating bodies are sufficient for communication and RF energy harvesting. Such frequency bands, are known as the 866 megahertz European ISM band, the 915 megahertz ISM band and the 2.4 gigahertz ISM band. For power transfer, a frequency of about 13.56 megahertz as specified in a common RFID band, provides a relatively high allowable field strength and high enough frequency to have efficient coupling to small structures. Regardless of the normal frequencies and power utilized for a particular application, when using a device on, in or near a biological organism, the various parameters may need to be tailored for safety.

Energy harvesting is a process hereby energy is derived from any number of external sources, captured and then stored for use. A typical example is an RFID system, wherein a radio transmitter broadcasts RF energy to power remote devices. The FCC and/or other similar regulatory agencies set forth specific guidelines for transmission, including power levels, which address various issues including safe levels of energy.

Figure 14:
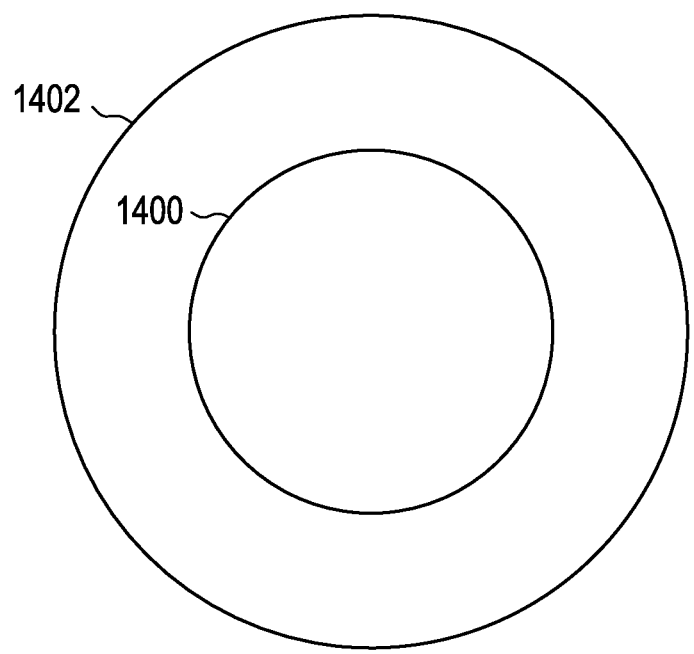
FIG. 14 is a simplified, diagrammatic representation of a contact lens and a single loop antenna in accordance with the present invention.

In an alternate exemplary embodiment, lenses may be constructed wherein the lens itself responds to the energization and de-energization of an antenna rather than use additional electronics. For example, an antenna 1400, as illustrated in FIG. 14, may be mounted in a lens 1402 in a manner such that when it is energized it may cause the lens 1402 to assume one specific shape and/or configuration and another or resting shape and/or configuration when it is de-energized. Its operation may be similar to the use of a piezoelectric material. The antennas 1400 may directly connect to an electro-optic lens such that the current induced in the antenna when energized by an external electromagnetic field coupled to the lens 1402 causes it to activate. Essentially, all that is required to implement such a system would be a convenient transmit power source and a receive antenna which may be implemented within the constraints of a contact lens. Preferably, only the antenna would be required with no additional tuning components.

It is important to note that any number of antenna designs and associated circuitry may be utilized in accordance with the present invention. The antenna of the present invention may be utilized for a number of applications, including actuation of other elements, including vision correction, dispensing therapeutic agents and photochromatic diming, charging onboard batteries and similar energy storage devices, continuous powering from a remote source and energy harvesting, transmitting data to and/or from the lens, and sensing on the eye itself. The transmission of data to and/or from the lens may include any type of information, including biometric data.

As described herein, the antennas may take on any number of forms, including traces on a circuit board, turns of wire embedded in the lens, printed on the lens and as a layer in a stacked die arrangement. Associated with the antennas are antenna related circuits. Radio frequency matching may be realized with discrete components, integrated circuits, integrated passive devices, MEMS tuners and switches. Resonating and load structures include parallel resistance to define the load and Q factor, series and/or parallel resonance, and tunable structures to adapt to the environment.

Any antenna designed preferably is designed to work on-body and be embedded in a saline environment with limited area and volume available. Accordingly, small magnetic loop devices are preferred, as monopoles and dipoles as well as similar antennas are not good on-body or in saline.

Any of the antennas set forth herein, e.g. coils, as well as any other antenna design may be realized using a fractal design, as is known in the relevant art, to optimize performance, including size, efficiency, input impedance, bandwidth and multiband usage. Essentially, a fractal antenna is any antenna structure that uses a fractal, self-similar design to maximize the length or increase the perimeter of a material that is able to transmit and/or receive electromagnetic radiation within a given total surface area or volume. Antenna tuning units are generally not required for use with fractal antennas due to their wide bandwidth and complex resonance.

As set forth herein and as it known in the art, antennas function by transmitting and/or receiving electromagnetic waves. There are a number of key factors which must be addressed in any antenna design and they include, gain, efficiency, impedance, bandwidth, polarization, directionality and radiation pattern. These factors are all important and can be varied depending on the application. For example, if an antenna is to be utilized in a contact lens, the antenna is preferably designed as a directional antenna with the bulk of radiated power travelling out of the eye and away from the head. Desired frequency and bandwidth may be selected or chosen depending on availability and desired functionality. Impedance, i.e. the voltage to current ratio at the input of the antenna may also be determined by the specific design.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens assembly comprising:
    a lens configured for placement in at least one of the inside of an eye or on the surface of an eye, the lens including an optic zone configurable for at least one of vision correction and vision enhancement and a peripheral zone;
    a stacked die structure comprising one or more substrate layers each having an upper and lower surface, the one or more substrate layers having an annular configuration;
    one or more mounting structures attached to at least one of the upper and lower surfaces of the one or more substrate layers;
    one or more electronic components attached to the one or more mounting structures, the electronic components configured to control the functionality of the lens; and
    at least one antenna arrangement operatively associated with the one or more electronic components and configured for at least one of the transmission of signals between the one or more electronic components and an external device, the reception of signals between the one or more electronic components on an external device, and inductive coupling, the at least one antenna arrangement being affixed to at least one of the upper and lower surfaces of the one or more substrate layers and isolated to reduce parasitic capacitance, wherein the stacked die structure, the one or more mounting structures, the one or more electronic components and the at least one antenna are encapsulated in the peripheral zone of the lens, the stacked die structure being configured to arrange the one or more substrate layers such that all components fit within the peripheral zone.

2. The ophthalmic lens assembly according to claim 1, wherein the lens comprises a contact lens.

3. The ophthalmic lens assembly according to claim 1, wherein the lens comprises an intraocular lens.

4. The ophthalmic lens assembly according to claim 1, wherein the lens comprises a spectacle lens.

5. The ophthalmic lens assembly according to claim 1, wherein the at least one antenna arrangement comprises one or more single-turn loop antennas.

* * * * *